(12) United States Patent
Pinns

(10) Patent No.: US 7,422,012 B2
(45) Date of Patent: Sep. 9, 2008

(54) APPARATUS AND METHOD FOR CONTROLLING UNPLEASANT HUMAN BREATH ODOR

(76) Inventor: Gary Pinns, 30612 Village Green Blvd., Warrenville, IL (US) 60555

( * ) Notice: Subject to any disclaimer, the term of this patent is extended or adjusted under 35 U.S.C. 154(b) by 653 days.

(21) Appl. No.: 11/032,443

(22) Filed: Jan. 10, 2005

(65) Prior Publication Data

US 2006/0154200 A1     Jul. 13, 2006

(51) Int. Cl.
*A61C 1/16* (2006.01)
(52) U.S. Cl. .............................. 128/200.12; 128/200.14; 128/200.23; 433/89
(58) Field of Classification Search ............ 128/200.14, 128/200.23, 200.12, 200.24; 433/80–89, 433/216; 601/162, 164; 604/151; 215/14
See application file for complete search history.

(56) References Cited

U.S. PATENT DOCUMENTS

| | | | | |
|---|---|---|---|---|
| 4,950,247 A | * | 8/1990 | Rosenblatt ................ | 604/181 |
| 5,295,830 A | * | 3/1994 | Shen et al. ................ | 433/116 |
| 5,755,572 A | * | 5/1998 | Bab et al. ................. | 433/80 |
| 6,129,547 A | * | 10/2000 | Cise et al. ................ | 433/80 |
| 6,164,967 A | * | 12/2000 | Sale et al. ................ | 433/80 |
| 6,659,768 B1 | * | 12/2003 | Ito et al. .................. | 433/95 |
| 6,766,549 B2 | * | 7/2004 | Klupt ....................... | 15/22.2 |

* cited by examiner

*Primary Examiner*—Steven O Douglas
(74) *Attorney, Agent, or Firm*—Wood, Phillips, Katz, Clark & Mortimer

(57) ABSTRACT

A method of controlling unpleasant human breath odor. The method includes the steps of: providing a breath treatment unit that is configured to be hand-holdable by a user; through the hand-holdable breath treatment unit, directing into the user's mouth a quantity of a breath treating substance; and discharging the breath treating substance through the hand-holdable breath treatment unit.

26 Claims, 3 Drawing Sheets

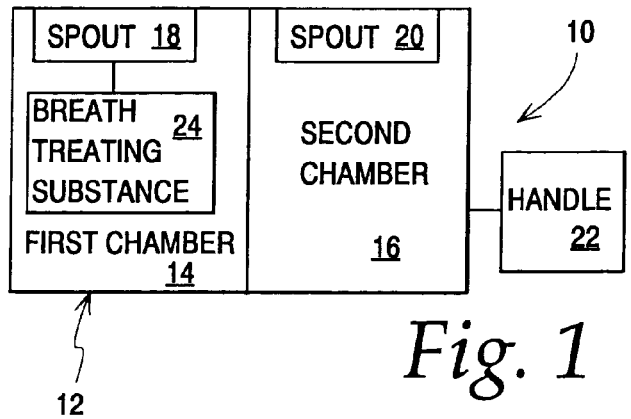
Fig. 1
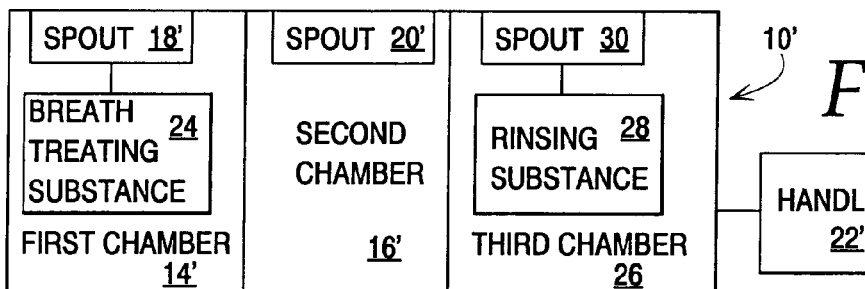
Fig. 3
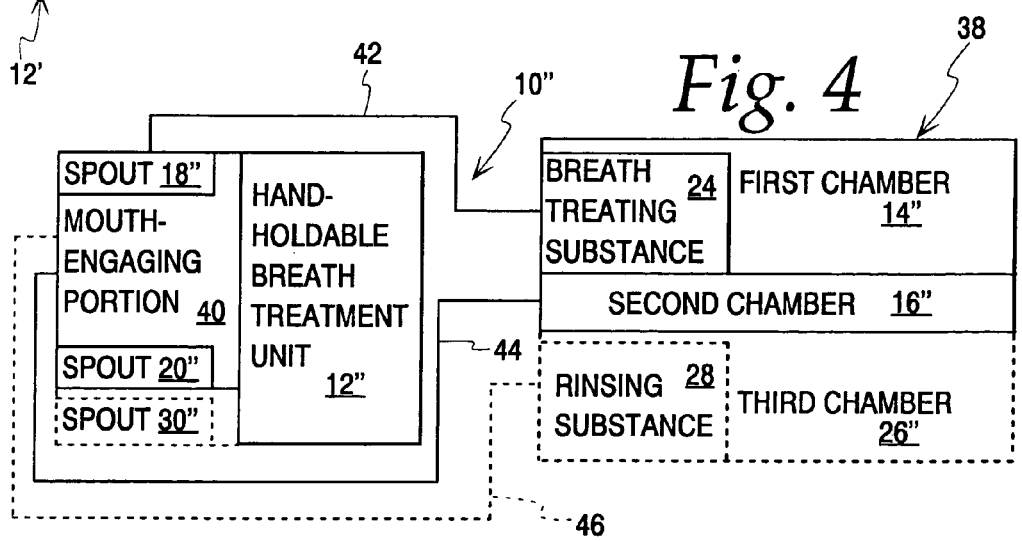
Fig. 2
Fig. 4

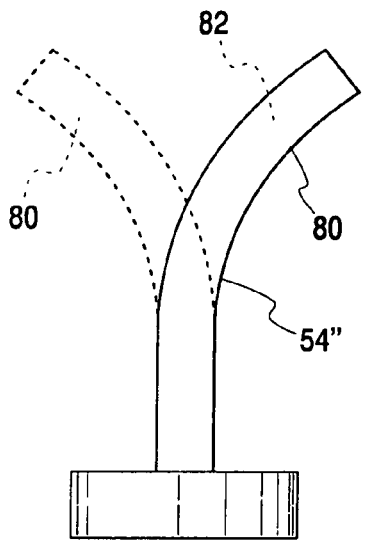
Fig. 10
Fig. 11
Fig. 12
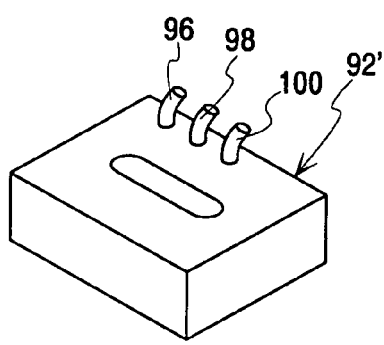
Fig. 13
Fig. 14
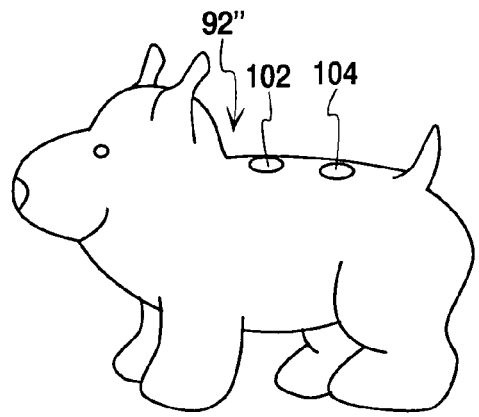
Fig. 15
Fig. 16

APPARATUS AND METHOD FOR CONTROLLING UNPLEASANT HUMAN BREATH ODOR

BACKGROUND OF THE INVENTION

1. Field of the Invention

This invention relates to a method and apparatus through which the user thereof may control the odor of his/her breath.

2. Background Art

The existence of unpleasant human breath odor is a persistent problem. "Bad breath", as it is commonly termed, is the source of much concern, and often embarrassment. Daily interactions, in both business and recreational environments, often place people in close face-to-face relationship such that breath odors can be sensed.

Purveyors of oral care products generally focus not only on dental health but on breath control. This concern has spawned myriad products, among which are tongue scrapers, toothpastes with special additives, mouthwashes, mints, pills, etc.

Despite the many attempts in the industry to control bad breath, some persons remain more prone to generating unpleasant breath odors than others. For these persons, breath control requires fairly regular maintenance, which may be carried out every couple of hours, or even more frequently. Most persons are prone to generating unpleasant breath odors, particularly after they have slept. The term "morning breath" is commonly used to identify breath with an unpleasant odor that one experiences after several hours of sleep.

While the oral care industry offers many different products to control bad breath, each has associated negative aspects. The use of small mints is convenient for an instantaneous "fix". However, mints generally have some drawbacks. First of all, mints commonly contain sugar which promotes tooth decay. Secondly, the mints function primarily as a mask of the odor and do not do anything to eliminate the bacteria that is the cause of the odor.

Generally, the most accepted way to address unpleasant breath odor is to gargle with any of a number of different mouthwashes that are on the market and promoted for this purpose. This process generally involves the intake of a quantity of a liquid mouthwash, gargling, expelling of the mouthwash, and a subsequent rinse process with water. For many, this is a common morning bathroom ritual after which the mouthwash and rinse product can be conveniently discharged into a sink.

The use of a mouthwash, while effective for a relatively significant period of time, is not practical before a spontaneous interaction, such as in the middle of the night. It is often "mood breaking" for two participants in such an encounter to separately move to a bathroom and gargle with mouthwash preparatory to an intimate interaction. Getting up to gargle is generally viewed as a chore when conducted in the middle of the night. As a result, individuals may be faced with the options of either foregoing the interaction, or interacting with unpleasant breath odors that may detract from the experience.

The use of breath mints, while offering a quick fix, generally will have an effect only for so long as the mint, or any residue therefrom, remains intact. There thus may be a progressive deterioration in the user's breath in a relatively short period of time.

The industry continues to search out products whereby spontaneous interaction of persons can be carried out without the existence of unpleasant breath odors and also without any significant inconvenience to the participants in such interaction.

SUMMARY OF THE INVENTION

In one form, the invention is directed to a method of controlling unpleasant human breath odor. The method includes the steps of: providing a breath treatment unit that is configured to be hand-holdable by a user; through the hand-holdable breath treatment unit, directing into the user's mouth a quantity of a breath treating substance; and discharging the breath treating substance through the hand-holdable breath treatment unit.

The method may further include the step of directing into the user's mouth, through the hand-holdable breath treatment unit, a quantity of a rinsing substance after the breath treating substance is discharged through the hand-holdable breath treatment unit.

The method may further include the step of reconfiguring the hand-holdable breath treatment unit after directing the breath treating substance into the user's mouth to allow the breath treating substance to be discharged through the hand-holdable breath treatment unit.

The method may include the step of reconfiguring the hand-holdable breath treatment unit after directing the breath treating substance into the user's mouth to allow the rinsing substance to be directed into the user's mouth.

In one form, the step of providing a hand-holdable breath treatment unit involves providing a hand-holdable breath treatment unit that contains a supply of a breath treating substance.

The step of providing a hand-holdable breath treatment unit may involve providing a hand-holdable breath treatment unit containing a supply of rinsing substance.

In one form, the step of providing a hand-holdable breath treatment unit involves providing a hand-holdable breath treatment unit with a chamber for receiving and confining breath treating substance that is discharged through the hand-holdable breath treatment unit.

The method may further involve the step of providing a remote unit. The step of directing into a user's mouth a quantity of breath treating substance may involve causing the breath treating substance to be communicated from the remote unit to and through the hand-holdable breath treatment unit.

The step of discharging the breath treating substance may involve discharging the breath treating substance through the hand-holdable breath treatment unit to the remote unit.

The method may further involve the steps of providing a discrete quantity of the breath treating substance in the hand-holdable treatment unit and disposing of the hand-holdable breath treatment unit after the discrete quantity of the breath treating substance is exhausted.

In one form, the step of directing a quantity of the breath treating substance into the user's mouth involves drawing a quantity of the breath treating substance into the user's mouth through suction.

In one form, the step of providing a hand-holdable breath treatment unit involves providing a hand-holdable breath treatment unit including a projection which can be placed in a user's mouth and through which at least one of a) the breath treating substance can be directed into the user's mouth and b) the breath treating substance can be discharged.

The step of providing a hand-holdable breath treatment unit may involve providing a hand-holdable breath treatment unit defining at least a part of a communication path for the breath treating substance that can be selectively placed in open and closed states.

The invention is further directed to an apparatus for controlling unpleasant human breath odor, which apparatus has a hand-holdable breath treatment unit through which a) a quantity of breath treating substance can be directed into a user's mouth and b) breath treating substance directed into a user's mouth can be controllably discharged.

In one form, the hand-holdable breath treatment unit is configured so that a quantity of a rinsing substance can be directed through the hand-holdable breath treatment unit into a user's mouth.

In one form, the hand-holdable breath treatment unit has separate first and second chambers for respectively containing a supply of the breath treating substance to be directed into a user's mouth and receiving and confining a breath treating substance that is discharged from a user's mouth.

In one form, the hand-holdable breath treatment unit has a projection that can be placed in a user's mouth and through which at least one of a) breath treating substance can be directed into the user's mouth and b) breath treating substance can be discharged.

In one form, the hand-holdable breath treatment unit defines at least a part of a communication path through the projection that can be placed selectively in open and closed states.

In one form, the apparatus further has a remote unit that is in communication with the hand-holdable breath treatment unit through which at least one of a) a breath treating substance can be directed to the hand-holdable breath treatment unit to be directed through the hand-holdable breath treatment unit into a user's mouth and b) a breath treating substance discharged by a user through the hand-holdable breath treatment unit can be received and confined.

In one form, the hand-holdable breath treatment unit is reconfigurable between first and second states and defines a first passageway. With the hand-holdable breath treatment unit in the first state, the first passageway communicates with the first chamber. With the hand-holdable breath treatment unit in the second state, the first passageway communicates with the second chamber.

The hand-holdable breath treatment unit may further include a third chamber. The hand-holdable breath treatment unit may have a third state, and with the hand-holdable breath treatment in the third state, the first passageway communicates with the third chamber.

The hand-holdable breath treatment unit may have first and second separate passageways that communicate respectively with the first and second chambers.

In one form, the hand-holdable breath treatment unit can be reconfigured to selectively block communication at least one of a) through the first passageway to the first chamber and b) through the second passageway to the second chamber.

In one form, the hand-holdable breath treatment unit can be reconfigured to selectively block communication through the first passageway with at least one of a) the first chamber with the hand-holdable breath treatment unit in the first state and b) the second chamber with the hand-holdable breath treatment unit in the second state.

The apparatus may further include a supply of breath treating substance in the first chamber.

A supply of breath treating substance may be provided in the first chamber, with a supply of a rinsing substance in the third chamber.

The hand-holdable breath treatments unit may be configured to simulate the appearance of a conventional decorative or functional object.

In one form, the first chamber is bounded by a replaceable liner element.

In one form, the hand-holdable breath treatment unit is configured so that the first chamber cannot be refilled by a user with breath treating substance.

In one form, the hand-holdable breath treatment unit is configured to be grasped as a unit in the hand of a user.

In another form, the hand-holdable breath treatment unit has a handle that can be grasped by a user.

In one form, the hand-holdable breath treatment unit has a mouth-engaging portion that is separable to facilitate cleaning and/or replacement of the mouth-engaging portion.

In one form, the hand-holdable breath treatment unit has a projection through which breath treating substance can be delivered to a user and discharged from a user's mouth. The projection can be configured and maintained in a plurality of different selected shapes to facilitate placement near or in a user's mouth.

BRIEF DESCRIPTION OF THE DRAWINGS

FIG. 1 is a schematic representation of one form of apparatus for controlling unpleasant human breath odor, according to the present invention, in the form of a self-contained, hand-holdable breath treatment unit with separate chambers, one of which is empty and the other of which contains a breath treating substance;

FIG. 2 is a schematic representation of a modified form of a hand-holdable breath treatment unit, as in FIG. 1, and including an additional chamber in which a rinsing substance is provided;

FIG. 3 is a flow diagram representation of one method for controlling unpleasant human breath odor, using the apparatus in FIG. 2;

FIG. 4 is a schematic representation of a further modified form of apparatus for controlling unpleasant human breath odor, according to the invention, and including a hand-holdable breath treatment unit and a separate, cooperating, remote unit in which the chambers, noted above, are formed;

FIG. 10 is a view as in FIGS. 7 and 8 of a further modified form of spout, according to the invention, and including a reconfigurable neck;

FIG. 11 is a schematic representation of a spout, according to the present invention, with a one-way valve associated therewith;

FIG. 12 is a schematic representation of a chamber on the inventive apparatus with a cartridge/liner incorporated, as to facilitate reuse;

FIG. 13 is a schematic representation of one form of housing on the inventive apparatus with integrally formed chambers;

FIG. 14 is a perspective view of a hand-holdable breath treatment unit, according to the present invention, and configured in the form of a conventional soda can;

FIG. 15 is a view as in FIG. 14 wherein the hand-holdable breath treatment unit is in the form of a tissue dispenser; and FIG. 16 is a view as in FIGS. 14 and 15 wherein the hand-holdable breath treatment unit is in the form of a toy/stuffed animal.

DETAILED DESCRIPTION OF THE DRAWINGS

Figure 5:
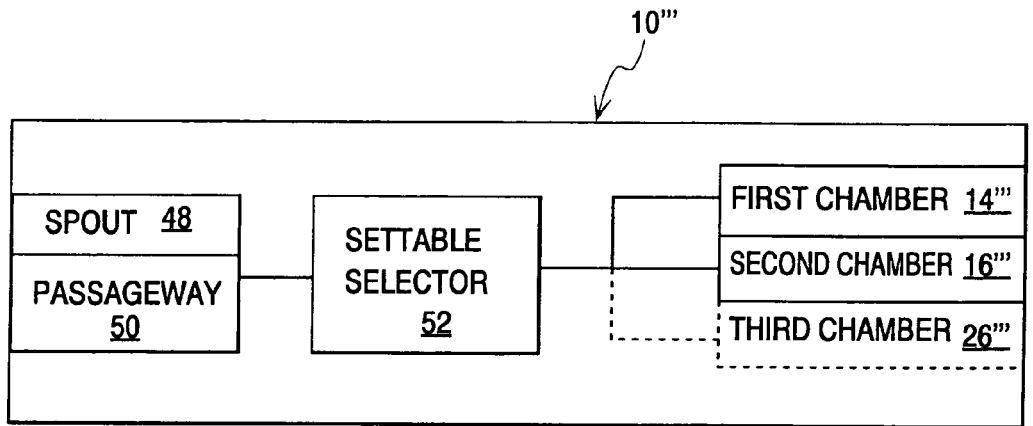
FIG. 5 is a schematic representation of another form of apparatus for controlling unpleasant human breath odor, according to the present invention and similar to that in FIG. 2, wherein a settable selector is incorporated to allow use of a single spout to selectively communicate with multiple chambers.

One form of apparatus for controlling unpleasant human breath odor, according to the present invention, is shown at 10. The apparatus 10 consists of a hand-holdable breath treatment unit 12 with a first chamber 14 and second chamber 16. A spout 18 communicates with the first chamber 14 and to externally thereof, with a like spout 20 communicating with the second chamber 16 and to externally thereof. The chambers 14, 16 may be defined by any suitable structure that is hand-holdable either by reason of having an overall configuration that allows the same to be grasped in a user's hand, or by reason of there being a handle 22 associated therewith that can be grasped by a user's hand. The spouts 18, 20 can take any configuration. The spouts 18, 20 may be simple openings in walls around the chambers 14, 16 or, more preferably, may each be in the form of a projection with a passageway therethrough.

A supply of a breath treating substance 24 is provided in the first chamber 14. A quantity of the breath treating substance 24 can be directed from the chamber 14 through the spout 18 into a user's mouth. The breath treating substance 24 may be a liquid or in a form, such as a powder, which facilitates pouring thereof, or drawing thereof as by suction, into the user's mouth. After the breath treating substance 24 is directed into the user's mouth, as to permit gargling, the user can conveniently discharge the same through the spout 20 into the second chamber 16, which accepts and confines the breath treating substance 24.

With this configuration, a user can conveniently maintain the apparatus 10 on hand, ready for use, as on a night stand. The apparatus 10 is conveniently manipulable by a user to both deliver, and discharge after use, the breath treating substance 24. The second chamber 16, which receives the used breath treating substance 24, can either be empty or contain some sort of a deodorizer to avoid generation of unwanted odor from the apparatus 10, after use thereof.

In FIG. 2, a modified form of apparatus, according to the present invention, is shown at 10'. The apparatus 10' has a hand-holdable breath treatment unit 12', defining first and second chambers 14', 16', corresponding in function to the chambers 14, 16 in FIG. 1, and additionally a third chamber 26. The third chamber 26 is designed to contain a supply of a rinsing substance 28. The first chamber 14' contains the breath treating substance 24, with the second chamber 16' being initially either empty or with some sort of a deodorizer, or the like. The rinsing substance 28 in the third chamber 26 can be directed into a user's mouth through a spout 30, that is either a simple opening in, or a projection from, a wall bounding the third chamber 26. The first and second chambers 14', 16' have associated spouts 18', 20', corresponding to the spouts 18, 20 in FIG. 1.

Preferably, the hand-holdable breath treatment unit 12' is configured and dimensioned so that it can be conveniently held by a single hand of user to facilitate use thereof. Alternatively, a handle 22', that is graspable by a user, can be provided to facilitate control of the apparatus 10'. The apparatus 10' is functionally the same as the apparatus 10, with the additional chamber 26 for storing, and allowing delivery of, the rinsing substance 28.

The apparatus 10' is used as follows, with reference to the flow diagram in FIG. 3, which represents one particular method of controlling unpleasant human breath odor, according to the present invention. As shown at block 32, the hand-holdable breath treatment unit 12' is provided in the initial step. Through the hand-holdable breath treatment unit 12', the breath treating substance 24 is directed into a user's mouth through the spout 18', as shown at block 34. As shown at block 36, after treatment with the breath treating substance 24, the user discharges the breath treating substance into the second chamber 16' through the spout 20'. Thereafter, the rinsing substance 28 is directed into the user's mouth through the spout 30, as shown at block 38, and ultimately discharged into its second chamber 16', as shown at block 39. The method is performed with the apparatus 10 in the same manner, with the exception that the rinsing substance 28 is not available in the apparatus 10.

In FIG. 4, a further modified form of apparatus for controlling unpleasant human breath odor, according to the present invention, is shown at 10''. The apparatus 10'' includes a hand-holdable breath treatment unit 12'', which functions in conjunction with a remote unit 38. In this embodiment, the remote unit 38 consists of a first chamber 14'', containing a supply of the breath treating substance 24, and a second chamber 16'' that is either empty or has a deodorizing substance, or the like, therein.

In this embodiment, the hand-holdable breath treatment unit 12'' is a separately manipulable unit that interacts with the remote unit 38. The remote unit 38 does not have to be carried with the hand-holdable breath treatment unit 12''. The hand-holdable breath treatment unit 12'' is shown to have a separate mouth-engaging portion 40 with separate spouts 18'', 20''. Through a conduit 42, the breath treating substance 24 is communicated to the mouth-engaging portion 40 from where it can be directed into the user's mouth through the spout 18''. The used breath treating substance 24 can then be discharged through the spout 20'' on the mouth-engaging portion 40 and is thereafter directed through a conduit 44 back into the second chamber 16''.

In this embodiment, the mouth-engaging portion 40 may be a separable unit that facilitates replacement and/or cleaning thereof. A like structure is contemplated as an option for all embodiments herein.

As shown in dotted lines in FIG. 4, the apparatus 10'' may optionally have a third chamber 26'' in which the rinsing substance 28 is contained for delivery through a conduit 46 to the mouth-engaging portion 44. The rinsing substance 28 is directed therefrom to a user's mouth through a spout 30''.

The nature of the conduits 42, 44, 46 is not critical to the present invention. Virtually any means of communicating flowable material is contemplated by the invention. As just one example, the conduits 42, 44, 46 may be formed from flexible tubing.

In FIG. 5, a further modified form of apparatus for controlling unpleasant human breath, according to the invention, is shown at 10'''. The apparatus 10''' has a self-contained, hand-holdable breath treatment unit 12''' that includes first, second and third chambers 14''', 16''', 26''', corresponding to the chambers described above. As shown in dotted lines, the third chamber 26''', while preferred, is optional.

The hand-holdable breath treatment unit 12''' has a spout 48 with an associated passageway 50. Through a settable selector 52, the hand-holdable breath treatment unit 12''' can be reconfigured to be selectively placed in first, second, and third states, wherein the passageway 50 is placed in communication with the first, second and third chambers 14''', 16''', 26''', to establish communication therethrough to the mouth of a user. The nature of the selector 52 is not critical to the present invention as there are myriad designs available to establish a communication path between the user's mouth, through the passageway 50, and selectively to any of the first, second and third chambers 14''', 16''', 26'''. Preferably, the selector 52 is settable through a user's mouth, by the tongue, or through the user's teeth in cooperation with a hand of the user that is engaging the hand-holdable breath treatment unit 12'''.

Figure 6:
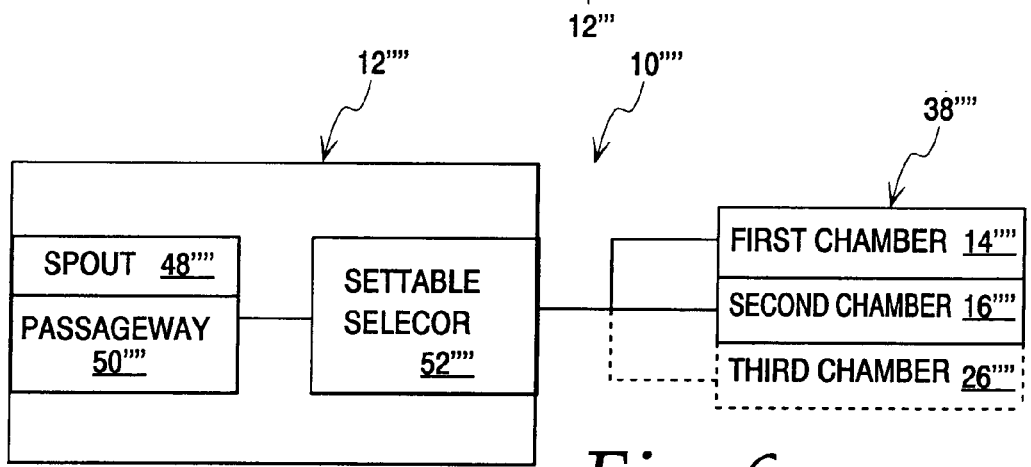
FIG. 6 is a view as in FIG. 5 wherein the apparatus consists of a hand-holdable breath treatment unit and a separate remote unit.

In FIG. 6, a further modified form of apparatus for controlling unpleasant human breath odor is shown at 10''''. The apparatus 10'''' consists of a hand-holdable breath treatment unit 12'''' and a separate remote unit 38''''. The remote unit 38'''' has first, second and third chambers 14'''', 16'''', 26''''. Through an appropriate mechanism, communication can be established between the first, second and third chambers 14'''', 16'''', 26'''' and a user's mouth through the hand-holdable breath treatment unit 12''''. In this embodiment, the hand-holdable breath treatment unit 12'''' has a spout 48'''' with a passageway 50'''' that can be selectively placed in communication with the first, second and third chambers 14'''', 16'''', 26'''' through a settable selector 52''''. The apparatus 10'''' otherwise functions in the same manner as the apparatus 10''', described with respect to FIG. 5. In this embodiment, the hand-holdable breath treatment unit 12'''' incorporates a settable selector 52'''', that is separate from the structure defining the chambers 14'''', 16'''', 26''''.

As a further alternative, the settable selector 52 could be formed independently of the hand-holdable breath treatment unit 12''' in FIG. 5. As a still further alternative, the settable selector 52'''' could be formed as a unit separate from the hand-holdable breath treatment unit 12'''' and remote unit 38''''. Other combinations of these components are contemplated by the invention.

The invention is described above in a schematic manner since the precise configuration of components is not critical to the invention. There are virtually a limitless number of different configurations and arrangements of components that can be devised consistent with the principles described above.

Figure 7:
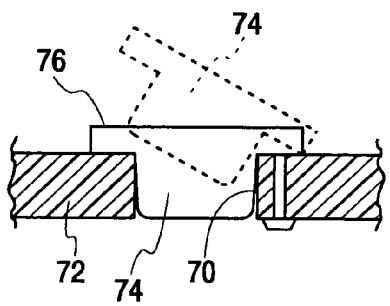
FIG. 7 is an elevation view of one form of closeable spout that can be used on the inventive apparatus.

As just one example, the construction of the spouts 18, 18', 18''; 20, 20', 20''; 30, 30''' 48, 48'''' could take virtually an unlimited number of different forms. One potential spout construction, which could be used for any of the above-noted spouts, is shown at 54 in FIG. 7. The spout 54 has a mounting portion 56 that might either be threadably attached to another part of its associated hand-holdable breath treatment unit, in the event that the same is intended to be removable, or permanently attached thereto. The mounting portion 56 has an associated projection 58, including an internal stopper 60 and a movable/slidable operator 62.

The operator 62 is slidable guidingly in the direction of the double-headed arrow 64 between open and closed positions. In the open position, flowable material, which may be either the breath treating substance 24 or rinsing substance 28, can flow in a passageway 66, defined by the spout 54, to and from a discharge opening 68. In the closed position, the stopper 60 blocks the discharge opening 68 so that the spout 54 is placed in a closed state. The construction of the spout 54 is representative of a number of spouts, used commonly on both disposable and reusable bottles, such as those used for water. The operator 62 is preferably configured so that it can be engaged, as by a user's teeth, to facilitate one-handed operation.

Figure 8:
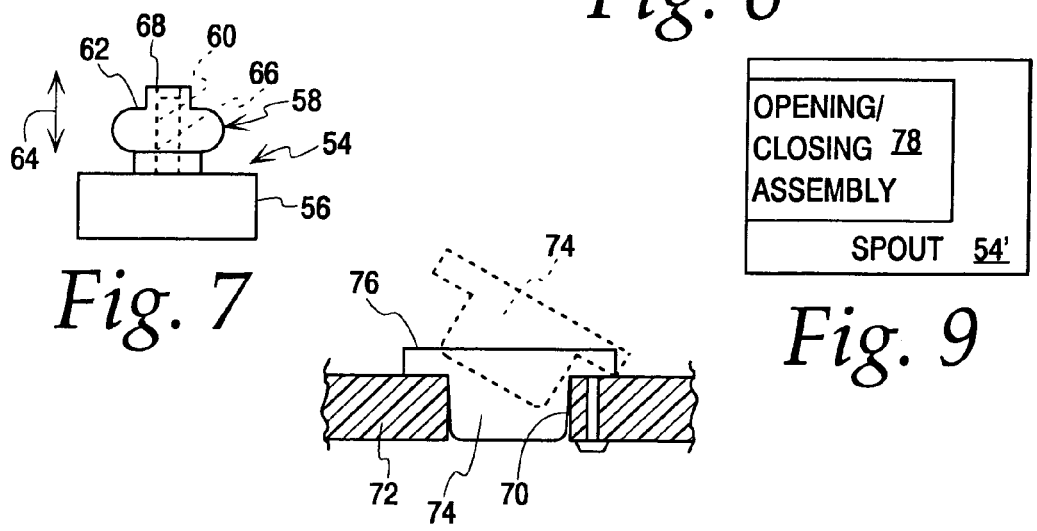
FIG. 8 is a fragmentary, cross-sectional view of a wall with which a stopper element is used to selectively close a spout passageway and with the stopper element shown in a closed position in solid lines and in an open position in dotted lines.

As shown in FIG. 8, as an alternative to a projection, the spout may define a passageway 70 that is a simple opening in a wall 72 that is selectively exposed and closed through a repositionable stopper 74. The stopper 74 has a tab 76 that can be grasped, as by a user's teeth, to reposition the stopper 74 from a closed state, shown in solid lines in FIG. 8, into an open state, shown in dotted lines in FIG. 8.

Figure 9:
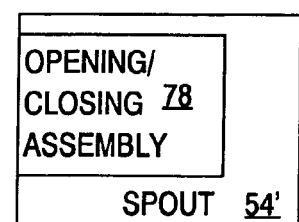
FIG. 9 is a schematic representation of a spout with an opening/closing assembly, according to the present invention.

As shown more generically in FIG. 9, the invention contemplates any type of spout 54', be it with or without a projection, and which may either be at all times in an open state or changeable in state through an opening/closing assembly 78.

As just one further example, as shown in FIG. 10, a spout 54'' is shown as a projection with an extended neck 80 that can be reconfigured and maintained in a plurality of selected different configurations. This likewise is a construction common to some water bottles, and the like. The neck 80 can be placed in a user's mouth and has an internal passageway 82 for communication of the breath treating substance 24 and rinsing substance 28. This construction facilitates use of the inventive apparatus with the user in virtually any orientation, including a prone orientation.

The inventive structure may be designed either for single use or for reuse. One dose, or multiple doses, of breath treating substance 24 and/or rinsing substance 28 may be provided. In FIG. 11, a spout 54''' is provided with a one-way valve 84 that may be provided for communication with one or separate chambers containing the breath treating substance 24 or rinsing substance 28. This one-way arrangement permits the breath treating substance 24 or rinsing substance 28 to be dispensed without allowing refilling of the associated chamber by a user.

Reuse may be permitted by refilling one or more chambers through an associated spout. Alternatively, as shown in FIG. 12, a chamber, intended to generically represent the first chambers 14', 14'', 14''', 14'''' and indicated at 86, has an associated cartridge/liner 88 for confining the breath treating substance 24. A like arrangement can be used for the chamber that holds the rinsing substance 28. Further, a liner 88 can be provided in any of the second chambers 16, 16', 16'', 16''', 16'''' to allow removal and disposal of the breath treating substance 24 and/or rinsing substance 28 that is discharged by the user into the second chamber 16, 16', 16'', 16''', 16''''.

The manner of forming the various hand-holdable breath treatment units 12, 12', 12'', 12''', 12'''' can vary significantly. As just examples, separate containers, each defining a chamber, may be united. Alternatively, a single housing 90, shown in FIG. 13, may have integrally formed first, second and third chambers $14^{5x'}$, $16^{5x'}$, $26^{5x'}$. Alternatively, the housing 90 may support individual cartridges/liners 88 defining one or more of these chambers.

The hand-holdable breath treatment unit may be made from any appropriate material, including wood, ceramic, metal, rubber, plastic, composite, etc. To allow the inventive structure to be present in a discrete manner, the hand-holdable breath treatment unit may be made to simulate the appearance of conventional ornamental or functional items. For example, as shown in FIG. 14, a hand-holdable breath treatment unit, generic to those identified above, is shown at 92 in the nature of a soda can, with a spout 94 that is in the form of a projection. The projecting form is not required.

In FIG. 15, a hand-holdable breath treatment unit 92' is shown in the form of a tissue container/dispenser with spouts 96, 98, 100, again each in the form of a projection.

In FIG. 16, a hand-holdable breath treatment unit 92'' is shown as a toy/stuffed animal with spouts in the form of openings 102, 104, each defining a communication passageway.

The objects depicted in FIGS. 14 through 16 are exemplary in nature only as there are a limitless number of shapes available for the inventive design.

The invention contemplates that all parts of the apparatus can be sealed so as to be "closed" in nature. This may be desirable to avoid spillage and/or odor emissions.

Many other variations are contemplated. One-way valves can be incorporated to avoid spillage. Active discharging mechanisms can be incorporated to facilitate delivery of the breath treating and rinsing substances 24, 28.

The foregoing disclosure of specific embodiments is intended to be illustrative of the broad concepts comprehended by the invention.

The invention claimed is:

1. A method of controlling unpleasant human breath odor, the method comprising the steps of:
   providing a breath treatment unit that is configured to be hand-holdable by a user in that the breath treatment unit is arranged to be grasped by a single hand of a user and that has separate supplies of breath treating substance and rinsing substance, the separate supplies of breath treating and rinsing substance contained within the hand-holdable breath treatment unit to be transportable with the hand-holdable breath treatment by a single hand of a user;
   through the hand-holdable breath treatment unit directing into the user's mouth a quantity of the breath treating substance from the supply of breath treating substance;
   discharging the breath treating substance through the hand-holdable breath treatment unit; and
   through the hand-holdable breath treatment unit directing into the user's mouth the rinsing substance from the supply of rinsing substance after the breath treating substance is discharged through the hand-holdable breath treatment unit.

2. The method of controlling unpleasant human breath odor according to claim 1 further comprising the step of reconfiguring the hand-holdable breath treatment unit after directing the breath treating substance into the user's mouth to thereby allow the breath treating substance to be discharged through the hand-holdable breath treatment unit.

3. The method of controlling unpleasant human breath odor according to claim 1 further comprising the step of reconfiguring the hand-holdable breath treatment unit after directing the breath treating substance into the user's mouth to allow the rinsing substance to be directed into the user's mouth.

4. The method of controlling unpleasant human breath odor according to claim 1 wherein the step of providing a hand-holdable breath treatment unit comprises providing a hand-holdable breath treatment unit that has at least three separate chambers to contain the separate supplies of breath treating substance and rinsing substance and discharged breath treating substance.

5. The method of controlling unpleasant human breath odor according to claim 1 wherein the step of providing a hand-holdable breath treatment unit comprises providing a hand-holdable breath treatment unit with a chamber for receiving and confining only the breath treating substance that is discharged through the hand-holdable breath treatment unit.

6. The method of controlling unpleasant human breath odor according to claim 1 further comprising the steps of providing a discrete quantity of the breath treating substance in the hand-holdable breath treatment unit and disposing of the hand-holdable breath treatment unit after the discrete quantity of the breath treating substance is exhausted.

7. The method of controlling unpleasant human breath odor according to claim 1 wherein the step of directing a quantity of the breath treating substance into the user's mouth comprises directing a quantity of the breath treating substance into the user's mouth through suction generated by the user.

8. The method of controlling unpleasant human breath odor according to claim 1 wherein the step of providing a hand-holdable breath treatment unit comprises providing a hand-holdable breath treatment unit comprising a spout which can be placed in a user's mouth through which at least one of a) the breath treating substance can be directed into the user's mouth and b) the breath treating substance can be discharged.

9. The method of controlling unpleasant human breath odor according to claim 8 wherein the step of providing a hand-holdable breath treatment unit comprises providing a hand-holdable breath treatment unit defining at least a part of a communication path for the breath treating substance that can be selectively placed in open and closed states.

10. An apparatus for controlling unpleasant human breath odor, the apparatus comprising:
    a breath treatment unit that is configured to be hand-holdable by a user in that the breath treatment unit is arranged to be grasped by a single hand of a user and through which quantities of a breath treating substance and rinsing substance can be selectively and separately directed into a user's mouth and through which breath treating substance directed into the user's mouth can be controllably discharged,
    the hand-holdable breath treatment unit comprising separate first and second chambers, with a supply of breath treating substance in the first chamber and a supply of rinsing substance in the second chamber, any breath treating and rinsing substances contained within the first and second chamber is movable by a single hand of a user with the hand-holdable breath treatment unit.

11. The apparatus for controlling unpleasant human breath odor according to claim 10 wherein the hand-holdable breath treatment unit comprises a projection that can be placed into a user's mouth and through which both a) breath treating substance can be directed into the user's mouth and b) breath treating substance can be discharged.

12. The apparatus for controlling unpleasant human breath odor according to claim 11 wherein the hand-holdable breath treatment unit defines at least a part of a communication path through the projection that can be placed selectively in open and closed states.

13. The apparatus for controlling unpleasant human breath odor according to claim 10 wherein the apparatus for controlling unpleasant human breath odor further comprises a remote unit that is in communication with the hand-holdable breath treatment unit through which a breath treating substance discharged by a user through the hand-holdable breath treatment unit can be received and confined.

14. The apparatus for controlling unpleasant human breath odor according to claim 10 wherein the hand-holdable breath treatment unit is reconfigurable between first and second states and defines a first passageway and with the hand-holdable breath treatment unit in the first state the first passageway communicates with the first chamber and with the hand-holdable breath treatment unit in the second state the first passageway communicates with the second chamber.

15. An apparatus for controlling unpleasant human breath odor, the apparatus comprising:
    a breath treatment unit that is configured to be hand-holdable by a user in that the breath treatment unit is arranged to be grasped by a single hand of a user and through which a quantity of a breath treating substance can be directed into a user's mouth and through which breath treating substance directed into the user's mouth can be controllably discharged, wherein the hand-holdable breath treatment unit comprises separate first and second chambers for respectively containing a supply of the breath treating substance to be directed into a user's mouth and receiving and confining breath treating substance that is discharged from a user's mouth, wherein the hand-holdable breath treatment unit is reconfigurable between first and second states and defines a first passageway and with the hand-holdable breath treatment unit in the first state the first passageway communicates with the first chamber and with the hand-holdable breath treatment unit in the second state the first passageway communicates with the second chamber, wherein the hand-holdable breath treatment unit comprises a third chamber, the hand-holdable breath treatment unit has a third state and with the hand-holdable breath treatment unit in the third state the first passageway communicates with the third chamber, wherein the hand-holdable breath treatment unit comprises a third chamber, the hand-holdable breath treatment unit has a third state and with the hand-holdable breath treatment unit in the third state the first passageway communicates with the third chamber, the supply of breath treating substance in the first chamber and any breath treating substance discharged by a user into the second chamber being movable by a single hand of a user with the hand-holdable breath treatment unit.

16. The apparatus for controlling unpleasant human breath odor according to claim 10 wherein the hand-holdable breath treatment unit comprises first and second separate passageways that communicate respectively with the first and second chambers.

17. The apparatus for controlling unpleasant human breath odor according to claim 16 wherein the hand-holdable breath treatment unit can be reconfigured to selectively block communication at least one of a) through the first passageway to the first chamber and b) through the second passageway to the second chamber.

18. The apparatus for controlling unpleasant human breath odor according to claim 15 wherein the hand-holdable breath treatment unit can be reconfigured to selectively block communication through the first passageway with at least one of a) the first chamber with the hand-holdable breath treatment unit in the first state and b) the second chamber with the hand-holdable breath treatment unit in the second state.

19. The apparatus for controlling unpleasant human breath odor according to claim 15 further comprising a supply of a breath treating substance in the first chamber and a supply of a rinsing substance in the third chamber.

20. The apparatus for controlling unpleasant human breath odor according to claim 10 wherein the hand-holdable breath treatment unit is configured to simulate the appearance of a conventional identifiable decorative or functional object.

21. The apparatus for controlling unpleasant human breath odor according to claim 10 wherein the first chamber is bounded by a replaceable liner element.

22. An apparatus for controlling unpleasant human breath odor, the apparatus comprising:

a breath treatment unit that is configured to be hand-holdable by a user in that the breath treatment unit is arranged to be grasped by a single hand of a user and through which a quantity of a breath treating substance can be directed into a user's mouth and through which breath treating substance directed into the user's mouth can be controllably discharged, wherein the hand-holdable breath treatment unit comprises separate first and second chambers for respectively containing a supply of the breath treating substance to be directed into a user's mouth and receiving and confining breath treating substance that is discharged from a user's mouth, wherein the hand-holdable breath treatment unit is configured so that the first chamber cannot be refilled by a user with breath treating substance, any supply of breath treating substance in the first chamber and any breath treating substance discharged by a user into the second chamber being movable by a single hand of a user with the hand-holdable breath treatment unit.

23. The apparatus for controlling unpleasant human breath odor according to claim 10 wherein the hand-holdable breath treatment unit is configured to be grasped as a unit, within which the chambers are defined, in the hand of a user.

24. The apparatus for controlling unpleasant human breath odor according to claim 10 wherein the hand-holdable breath treatment unit has a handle that can be grasped by a user.

25. The apparatus for controlling unpleasant human breath odor according to claim 10 wherein the hand-holdable breath treatment unit has a mouth-engaging portion that is separable to facilitate cleaning and/or replacement of the mouth-engaging portion.

26. The apparatus for controlling unpleasant human breath odor according to claim 10 wherein the hand-holdable breath treatment unit has a projection through which breath treating substance can be delivered to a user and discharged from a user's mouth and the projection can be reconfigured and maintained in a plurality of different selected shapes to facilitate placement near or in a user's mouth.

\* \* \* \* \*